United States Patent [19]

Wanamaker

[11] Patent Number: 4,984,580
[45] Date of Patent: Jan. 15, 1991

[54] BLOOD DRAWING APPARATUS

[76] Inventor: Thomas Wanamaker, R.R. #2, P.O. Box 619, Kansas City, Mo. 64111

[21] Appl. No.: 297,613

[22] Filed: Jan. 17, 1989

Related U.S. Application Data

[62] Division of Ser. No. 854,171, Apr. 21, 1986, Pat. No. 4,841,985.

[51] Int. Cl.$^5$ .............................................. A61B 5/00
[52] U.S. Cl. ..................................... 128/763; 128/770; 604/240
[58] Field of Search ...................... 128/763, 764, 770; 604/52, 187, 240, 242, 262, 272, 413

[56] References Cited

U.S. PATENT DOCUMENTS 4,154,229  5/1979  Nugent ............................... 128/764
4,846,808  7/1989  Haber et al. ........................ 128/763

FOREIGN PATENT DOCUMENTS 771890  10/1934  France ................................ 128/763

Primary Examiner—Max Hindenburg
Attorney, Agent, or Firm—Michael Yakimo, Jr.

[57] ABSTRACT

A blood sample device for drawing blood from the patient. The device includes a locking mechanism which holds a biased needle assembly in the needle holder during use. Upon release of the locking mechanism, the bias on the needle assembly ejects the same from the holder. Various embodiments of locking mechanisms, utilized with and without various bias means, are utilized.

4 Claims, 6 Drawing Sheets

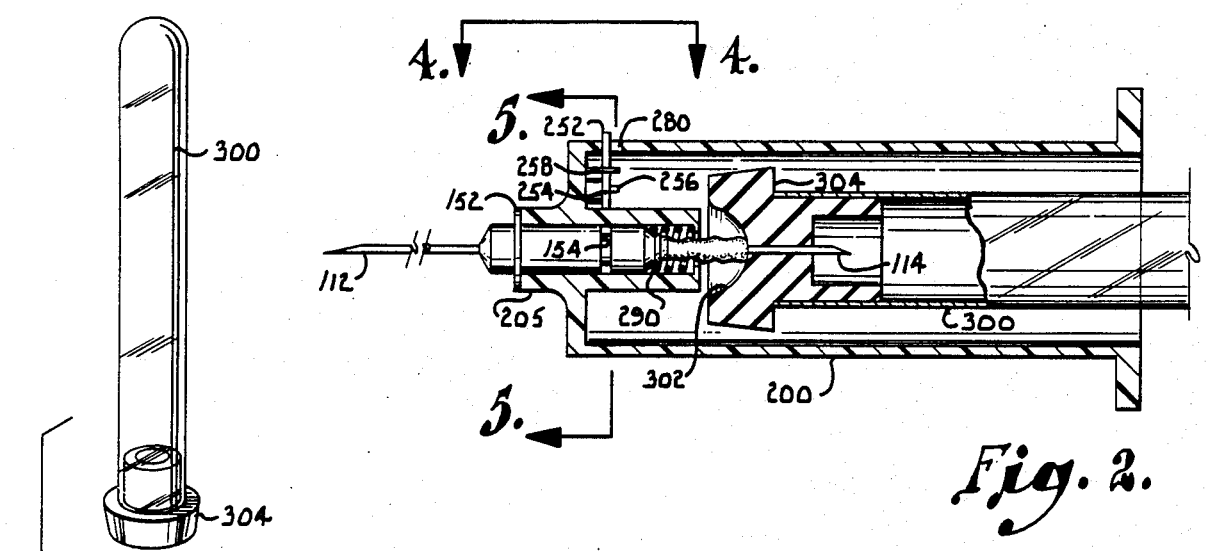
Fig. 2.
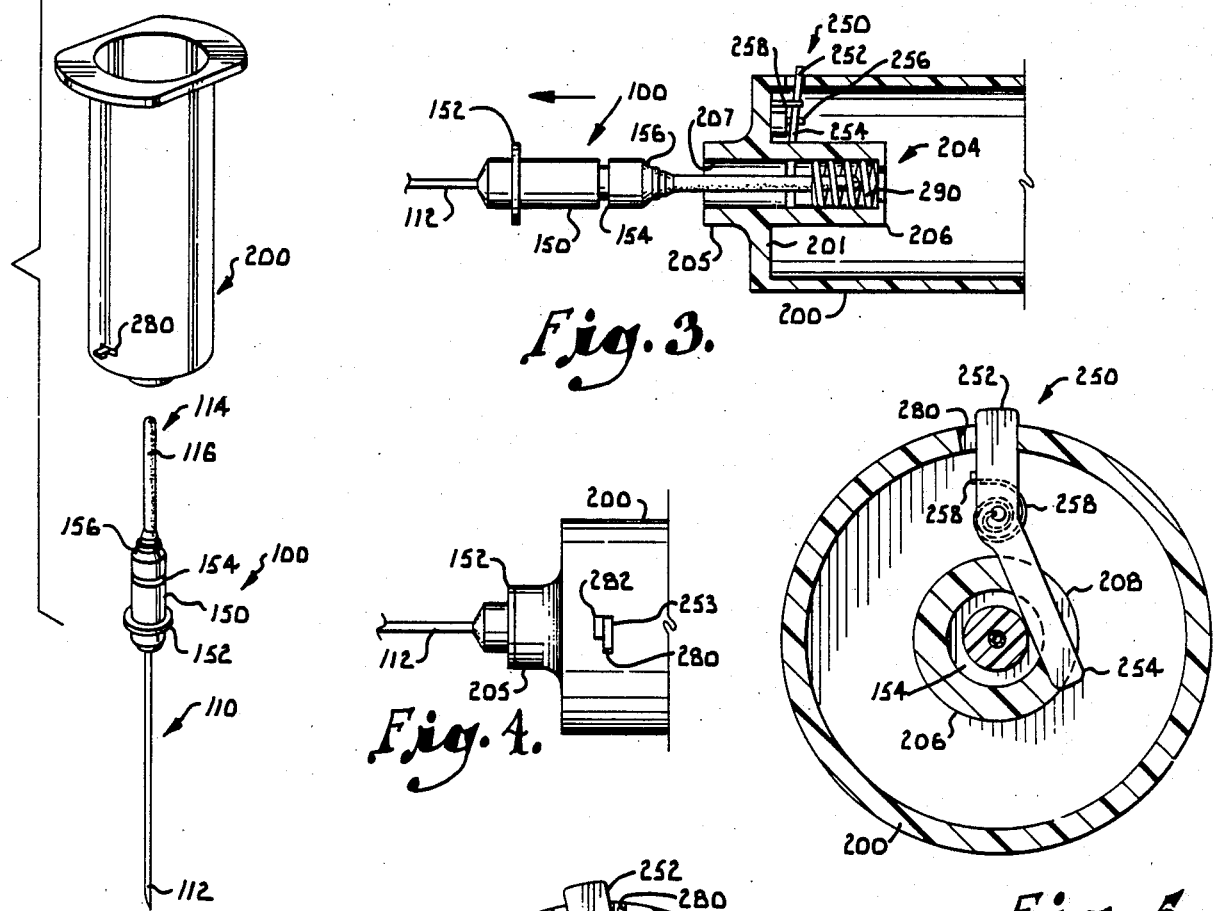
Fig. 3.
Fig. 4.
Fig. 5.
Fig. 1.
Fig. 6.

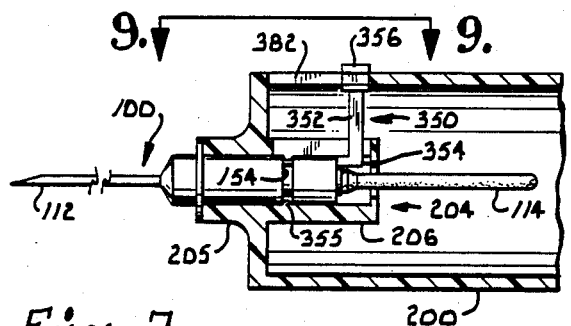
Fig. 7.
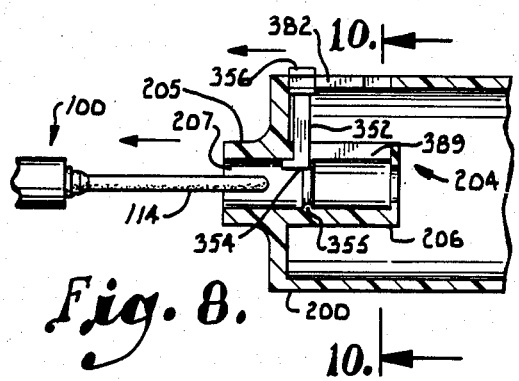
Fig. 8.
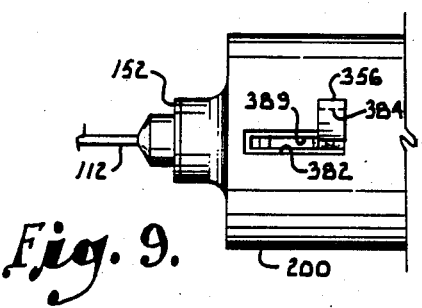
Fig. 9.
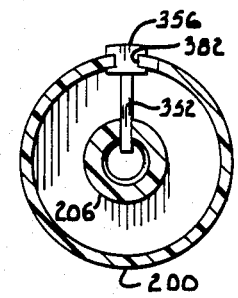
Fig. 10.
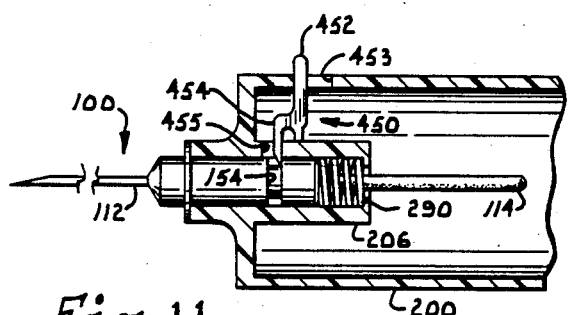
Fig. 11.
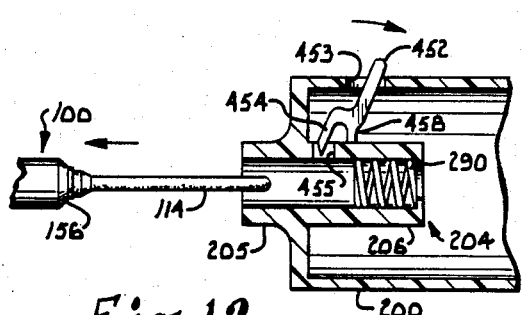
Fig. 12.
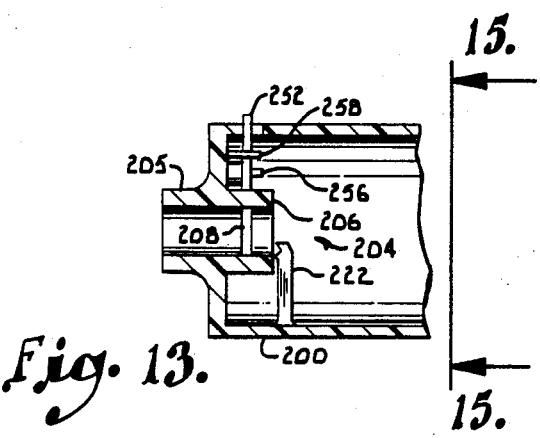
Fig. 13.
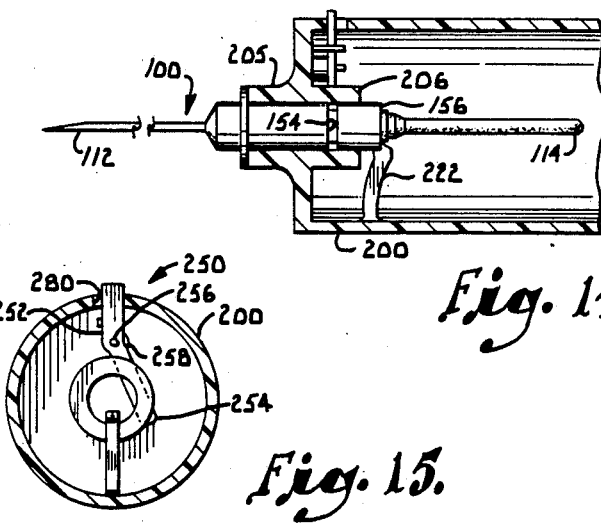
Fig. 14.
Fig. 15.

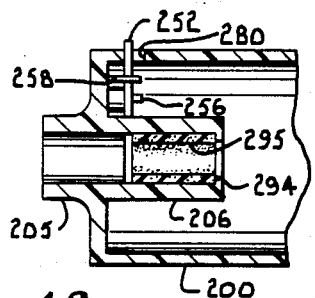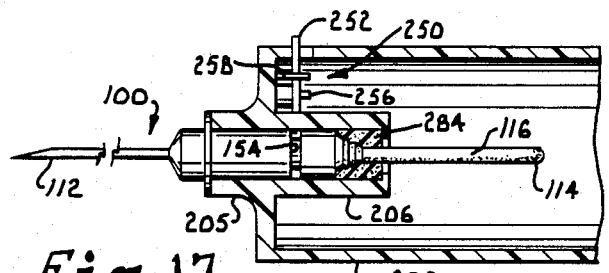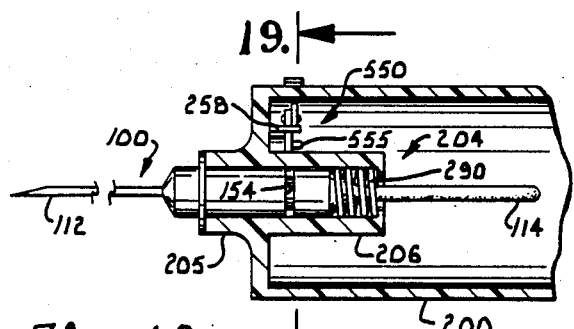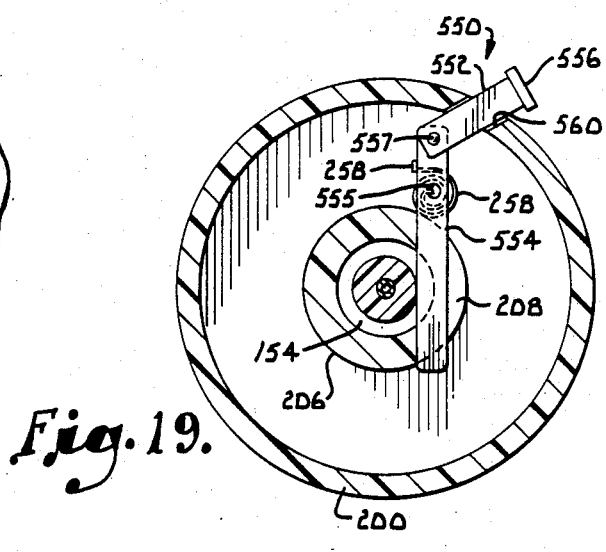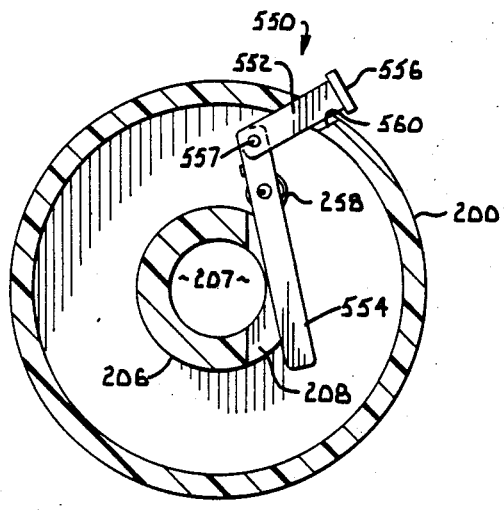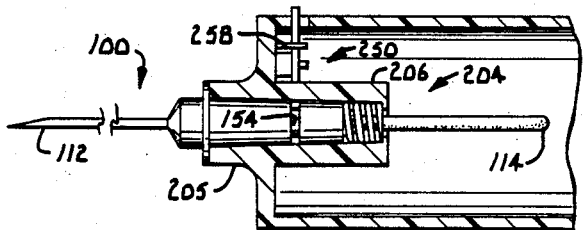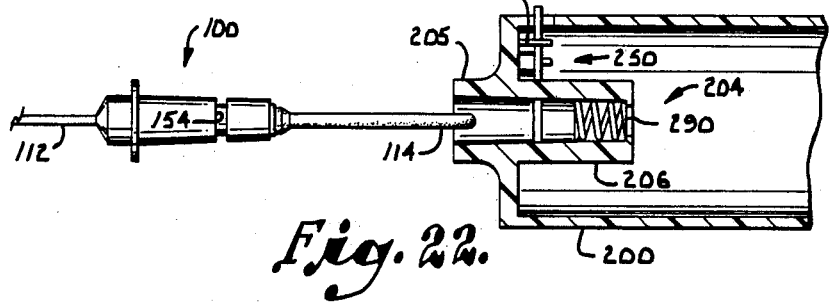

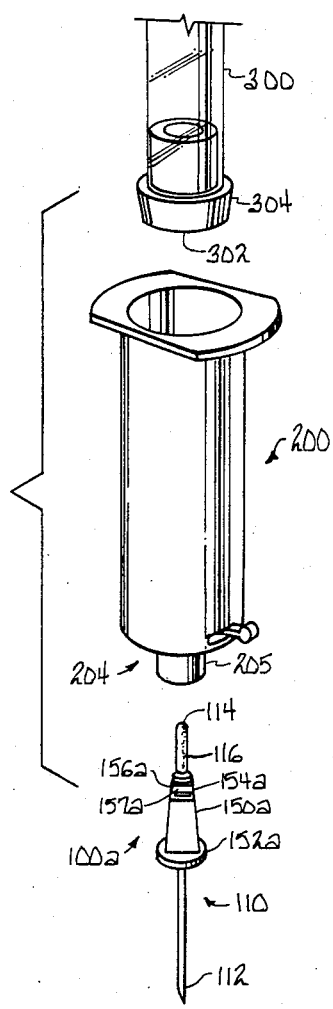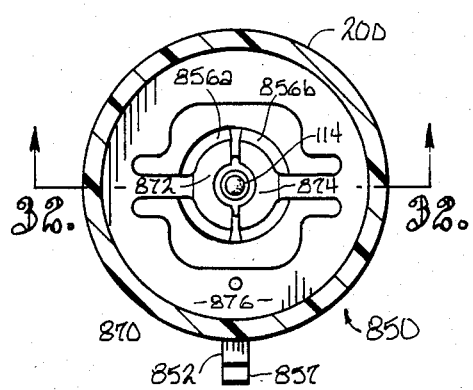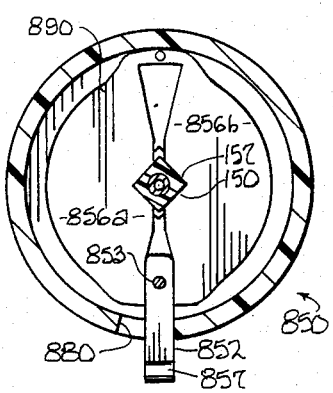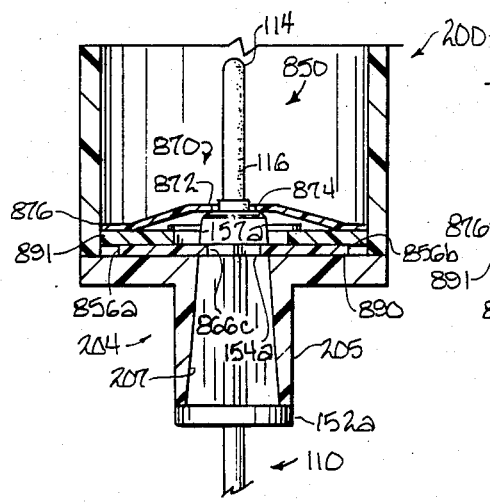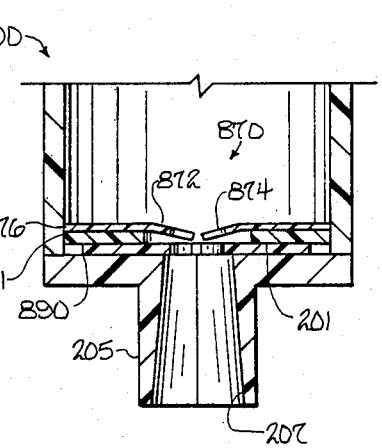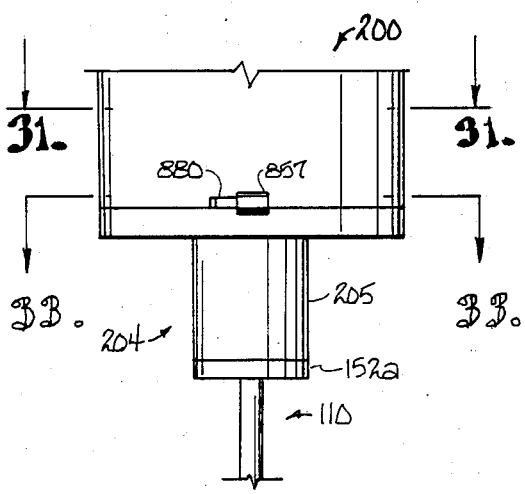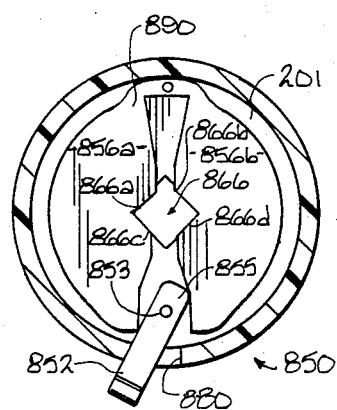

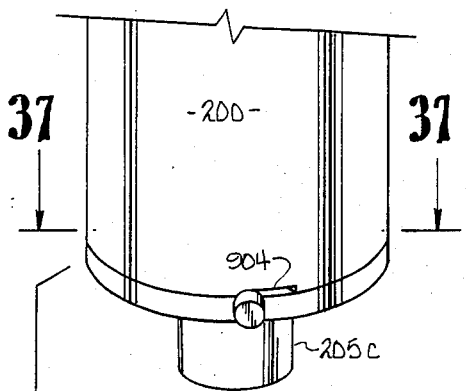
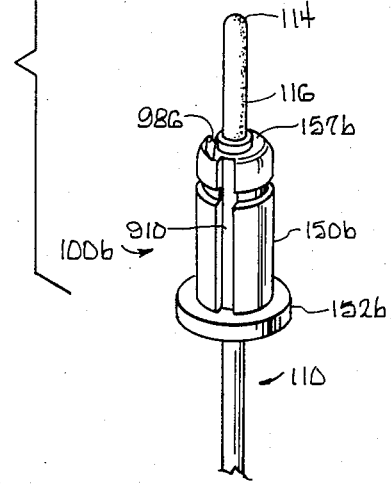
Fig. 36.
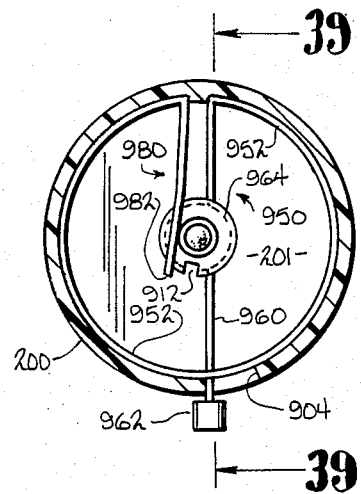
Fig. 37.
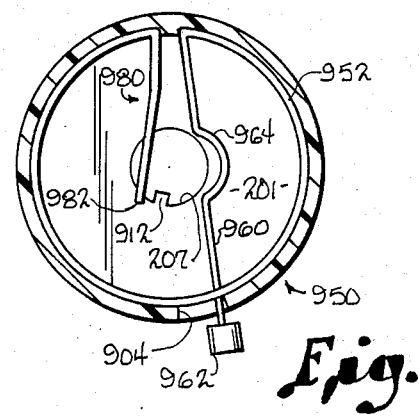
Fig. 38.
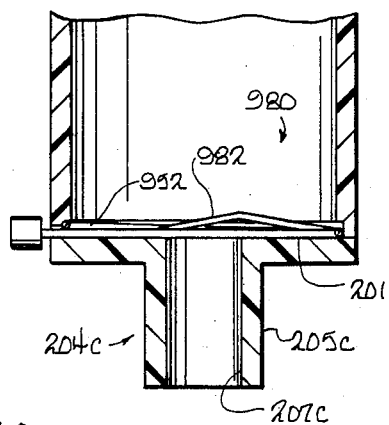
Fig. 40.
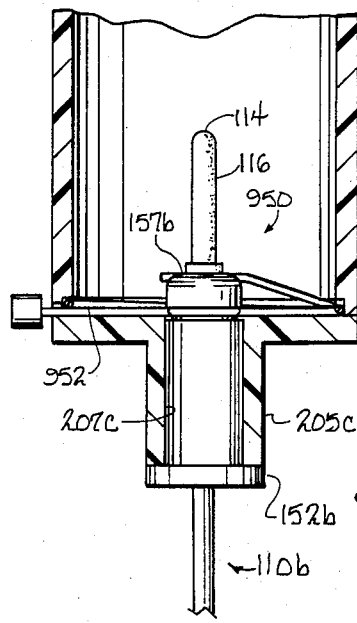
Fig. 39.

BLOOD DRAWING APPARATUS

This application is a division of application Ser. No. 06/854,171 filed Apr. 21, 1986 now U.S. Pat. No. 4,841,985.

BACKGROUND OF THE INVENTION

This invention pertains to a blood sampling device and more particularly to apparatus which reduces the possibility of risk of contamination by diseased blood to the user.

The analyses of a patient's blood is an important tool used in diagnosis. The blood is drawn from the patient by the use of various syringe-type apparatus. Blood collection devices utilize a needle inserted into the vein of the patient; i.e. venipuncture, so as to draw the blood through the needle and into an associated collection reservoir.

In light of the recent AIDS problem, attention has been directed to the risk of contamination of the blood drawer/user due to contact with the blood of a diseased patient. Contamination may occur either through the user being punctured by a used needle upon its removal from the blood collection device and/or the splashing of the blood onto the user during such removal.

The use of various blood collection devices are common in the art. One device generally comprises a needle holder, a needle assembly and an evacuated blood collection tube. The needle assembly is threadably engageable with the needle holder and presents a front end for puncturing the vein of the patient and a rear end for insertion into an evacuated collection tube.

The evacuated tube causes the blood to be drawn from the patient, via the venipunctured front end, and discharged into the collection tube from the rear end. As the disposal of the used needle assembly requires manual handling by the user, the possibility of skin puncture and an undesired transfer of diseased blood into the user arises. Also, diseased blood may splash onto the user during removal.

In response thereto, I have invented a needle holder/needle assembly which eliminates the need for the user to manually handle the needle assembly subsequent to blood purging. My now preferred embodiments releasably connects/locks a biased needle assembly with the needle holder and blood collection tube. Subsequent to blood withdrawal, the user operates a locking mechanism so that the biased needle assembly is released-/ejected from the needle holder. The released needle assembly may then be directed into a waste receptacle for subsequent disposal. Thus, the user does not manually handle the needle assembly subsequent to its use. I have herein disclosed various embodiments of locking and bias means utilized in connection with my invention.

It is therefor a primary object of this invention to provide for an improved blood collection device which reduces the risk of contamination to users.

Another general object of this invention is to provide for a blood collection device, as aforesaid, which particularly reduces the risk of contamination upon disposal of the utilized needle.

Still another general object of this invention is to provide for a blood collection device, as aforesaid, which precludes the need for the user to manually handle the needle assembly after use.

Another object of this invention is to provide a blood collection device, as aforesaid, which utilizes a needle assembly releasably engageable with a needle holder.

A further object of this invention is to provide a blood collection device, as aforesaid, which utilizes a needle assembly releasably engageable with a needle holder.

A further object of this invention is to provide a blood collection device, as aforesaid, which utilizes a bias on the needle assembly to urge removal of the needle assembly from the associated needle holder.

Other objects and advantages of this invention will become apparent from the following description taken in connection with the accompanying drawings, wherein is set forth by way of illustration and example, an embodiment of this invention.

BRIEF DESCRIPTION OF THE DRAWINGS

FIG. 1 illustrates an exploded, perspective view of one embodiment of the blood collection device;

FIG. 2 is a medial, sectional view, taken along the medial centerline of the device of FIG. 1, illustrating the elements of FIG. 1 in position for use;

FIG. 3 is a fragmentary, sectional view of the device, as shown in FIG. 2, illustrating the ejection of the needle assembly from its housing and holder;

FIG. 4 is a side view, taken along lines 4—4 in FIG. 2, illustrating the needle locking assembly and lever in a locked position;

FIG. 5 is a sectional view, taken along lines 5—5 in FIG. 2 and on an enlarged scale, illustrating the biased engagement of the locking lever with the locking slot of the needle assembly;

FIG. 6 is a fragmentary, sectional view, as shown in FIG. 5, illustrating the locking lever in a released position with a portion of a lever arm removed to show the underlying return spring;

FIG. 7 illustrates an alternative, slidable locking lever bearing against the needle assembly as held in place by an annular rim engaging the locking slot of the needle assembly;

FIG. 8 is a fragmentary, sectional view illustrating the movement of the locking lever of FIG. 7 to a released position and concurrent ejection of the needle assembly;

FIG. 9 is a plan view, taken along lines 9—9 in FIG. 7, illustrating the locking lever of FIG. 7 in a locked position;

FIG. 10 is a sectional view, taken along lines 10—10 in FIG. 8, illustrating the relationship of the locking lever with the housing for the needle assembly;

FIG. 11 is a sectional, horizontal view showing an alternative locking structure as maintaining the biased needle assembly with its housing;

FIG. 12 is a sectional view illustrating the structure of FIG. 11 in a released position and the ejected needle assembly from its housing;

FIG. 13 is a fragmentary, sectional view illustrating an alternative embodiment for presenting a bias against the needle assembly as used with the locking lever of FIG. 1-6;

FIG. 14 is a sectional view illustrating the structure of FIG. 13 offering its bias against an engaged needle assembly;

FIG. 15 is a sectional view, taken along lines 15-15 in FIG. 13, illustrating the relationship of the leaf spring bias of FIGS. 13 and 14 and locking mechanism with the housing of the needle assembly;

FIG. 16 is a fragmentary, sectional view illustrating the use of a compressible material within the housing of the needle assembly for biasing the same;

FIG. 17 is a sectional view illustrating the compression of the FIG. 16 material upon engagement of the needle assembly within its housing;

FIG. 18 is a sectional view illustrating an engaged needle assembly as maintained by the alternative locking lever further illustrated in FIGS. 19 and 20;

FIG. 19 is a sectional view, taken along lines 19—19 in FIG. 18 and on an enlarged scale, illustrating an alternative, pushbutton locking mechanism in an engaged/locking position;

FIG. 20 is a view as in FIG. 19 illustrating the pushbutton locking mechanism in a disengaged/released position;

FIG. 21 is a fragmentary, sectional view illustrating an alternative, tapered housing for receiving a tapered needle assembly therein;

FIG. 22 is a fragmentary, sectional view illustrating the ejection of the needle assembly from the tapered housing;

FIG. 29 illustrates an exploded, perspective view of an alternative embodiment of the blood collection device;

FIG. 30 is an enlarged fragmentary view of the lower end of the device of FIG. 29 with the cannula structure in place within the housing;

FIG. 31 is a sectional view, taken along line 31—31 in FIG. 30, illustrating the bias ring atop the locking ring with the rear end of the cannula structure extending therethrough;

FIG. 32 is a sectional view, taken along line 32—32 in FIG. 31, illustrating the cannula structure locked within the housing and the spring bias tabs in a displaced position;

FIG. 33 is a sectional view, taken along line 33—33 in FIG. 30, illustrating the locking ring in a normal/relaxed position engaging the locking hub of the cannula structure;

FIG. 34 is a sectional view, similar to that of FIG. 33, but illustrating the locking ring in an unlocked position with the cannula structure being displaced from its housing;

FIG. 35 is a sectional view, similar to that of FIG. 32, but illustrating the locking ring/bias ring and tabs thereof normally in a relaxed position;

FIG. 36 illustrates an exploded, perspective view of an alternative embodiment of the blood collection device;

FIG. 37 is a sectional view of FIG. 36 illustrating a relaxed locking arm;

FIG. 38 is a sectional view of FIG. 36 illustrating a displaced locking arm;

FIG. 39 is a sectional view of FIG. 36 illustrating a cannula structure locked within the housing;

FIG. 40 is a sectional view of FIG. 36 illustrating the bias arm in a unlocked position with the cannula structure being displaced from its housing.

DESCRIPTION OF THE PREFERRED EMBODIMENT

Figure 23:
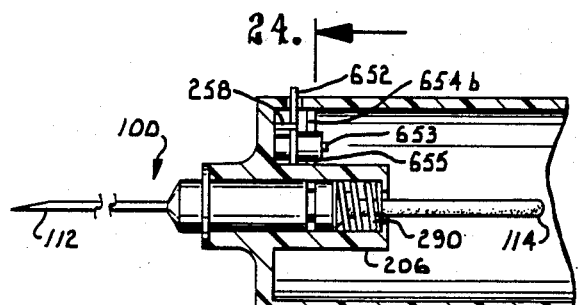
FIG. 23 is a fragmentary, sectional view illustrating an engaged needle assembly as maintained by a cam-type locking mechanism further illustrated in FIGS. 24-25.

Turning more particularly to the drawings, FIG. 1 illustrates a first embodiment of a blood collection device as generally comprising a needle assembly 100, a needle holder 200 and an evacuated sample collection tube 300.

The needle assembly generally comprises a cannula 110 having a front end 112 for venipuncture and a covered 116 rear end 114 for insertion through a membrane 302 of the stopper 304 of tube 300. A removable cover (not shown) encloses the front end 112 of the needle 110 prior to use. An intermediate hub 150 surrounds needle 110 and includes a stop ring 152 and an annular locking slot 154.

The needle holder 200 is generally cylindrical in configuration for receiving the evacuated collection tube 300 therein. Preferably integral with the holder 200 is a front, exterior boss 205 and a colinear, interior boss 206 which cooperate to present a needle housing generally designated as 204. Bore 207 within housing 204 allows for slidable insertion of the hub 150 and rear end 116 of the needle assembly 100 therein.

A slot 208 within the wall of the interior boss 20 allows for insertion of an arm 254 of locking lever assembly 250 therein. The locking lever assembly 250 includes integral first 252 and second 254 arms rotatably mounted about a pivot pin 256 extending from the interior base 201 of the holder 200. Lever arm 254 is spring-biased 258 into a position extending through slot 208 and into the bore 207. The free end of the arm 252 extends through a slot 280 in the wall of the needle holder 200.

Upon insertion of the needle assembly 100 into bore 207 of housing 204, the cannula rear end !14 extends through the coils of spring 290 and through the membrane 302 of the tube 300 stopper 304. Upon insertion, the cover 116 of the rear cannula end 114 is pushed back so as to expose the rear end 114 of the cannula 110 within the tube 300 as shown in FIG. 2. The rearward projection of the needle assembly 100 through housing 204 is delimited by abutment of stop member 152 with the front edge of boss 205.

Upon insertion, the rear surface 156 of hub 150 compresses the spring 290 located within the housing. Concurrently, the biased 258 second arm 254 engages the annular locking slot 154 surrounding hub 150. This arm 254/slot 154 engagement overcomes the bias offered by the compressed spring 290 against the hub 150 of the needle assembly 100. Such engagement maintains the needle assembly 100 within housing 204 and in a functional position for use.

The front end 112 of the cannula is then inserted by the blood drawer/user into the patient's vein. The evacuated tube 300 draws the blood through the front end 112 of cannula 110 for ultimate discharge into the sample tube 300 via the rear cannula end 114.

Subsequent to drawing the desired blood sample, disposal of the needle assembly 100 is required. The user pushes the tab 253 at the end of the arm 252 out of the notch 282 in the slot 280. (The engagement of a portion of the arm 252 within notch 282 precludes undesirable movement of arm 252 during use of the device.) Subsequent user-movement of arm 252 along slot 280 pivots the biased second arm 254 away from its locking position within the locking slot 154 (FIG. 6). Once disengaged, the bias offered by the compressed spring 290 ejects the needle assembly 100 from the housing 204. Upon user-release of tab 253, the arm 254 is spring 258 biased into its FIG. 5 position. Accordingly, the user need not handle the needle assembly 100 subsequent to blood withdrawal.

FIGS. 7-10 illustrate an alternative embodiment for locking the needle assembly 100 within its housing 204. A slidable lever 350 comprises a first arm 352 and a second arm 354 normal thereto. A tab 356 at the end of the first arm 352 slidably engages an elongated slot 382 in the side of the needle holder 200. The end of arm 352 extends through an elongated slot 389 in the wall of boss 206 so that arm 354 extends into bore 207 of housing 204. Upon insertion of the needle assembly into its functional position (FIG. 7) within housing 204, the locking slot 154 engages an annular rim 355 extending about the interior of the boss 206 of the housing 204. This rim 355/slot 154 engagement maintains the needle assembly 100 in place for use.

As shown in FIG. 9, tab 356 is slidable into a notch 384 of the elongated slot 382. This tab 356/notch 384 relationship maintains the lever assembly 350 in place during use. Subsequent to use, tab 356 is user-slidable along the elongated slot 382 along with the arm 354 along slot 389. The pressure of arm 354 against the rear surface 156 of hub 150 releases the locking rim 155 from the locking slot 154 and subsequently urge the needle assembly 100 from its housing 204.

FIG. 11 illustrates an alternative embodiment of a locking lever 450 for engagement with the locking slot 154. A flexible lever 450 is attached to the boss 206 via post 458 and includes a user-operable arm 452 extending through slot 453 in holder 200. Protrusion of the prong-type locking arm 454 through the slot 455 in boss 206 engages the locking slot 154 of the needle assembly 100 upon its insertion into housing 204. This engagement overcomes the spring 290 bias so as to maintain the needle assembly 100 in place for use. Upon user-operable movement of the arm 452 within slot 453, as shown in FIG. 12, the locking arm 454 is released from the locking slot 154 s that the spring bias 290 ejects the needle assembly 100 from its housing 204.

FIGS. 13-15 illustrates, in connection with locking lever assembly 250, the use of a flexible leaf-type spring 222 bias against the needle assembly 100. The tensioned spring 222 extends from the interior wall of holder 200 and bears against the rear surface 156 of the hub 150 when the needle assembly 100 is inserted into housing 204. The bias offered by the leaf-type spring 222 is overcome by the arm 254/slot 154 combination as shown in FIGS. 1-6 and 15. As such, the leaf spring 222 is urged away from its normal position (FIG. 14). Upon release of the locking lever 250 from slot 154, as above-described, the leaf-type spring 222 returns to its normal position (FIG. 13) so as to urge the unlocked needle assembly 100 from its housing 204. The use of a resilient material for spring 222 will return the same to its FIG. 13 position.

FIGS. 16 and 17 illustrate, in connection with the locking lever assembly 250, the use of a compressible material 294, such as polyurethane, as the bias against the needle assembly 100. The compressible material 294 is shown as inserted into the bore 207 of the housing 204. A bore 295 extends through such material 294 to allow for projection of the rear cannula end 114 therethrough. Upon insertion of the needle assembly 100 within housing 204, the biased 258 arm 254 engages the locking slot 154 and holds the needle assembly in place for use. Concurrently, the material 294 is compressed, as shown in FIG. 17, so as to offer a bias against the needle assembly 100. Subsequent to use, user-operation of the locking lever 250, as above-described, disengages arm 254 from slot 154. Thus, the material 294 expands to its normal position causing ejection of the needle assembly 100 from its housing.

FIGS. 18-20 illustrate a pushbutton-type of locking lever assembly 550 used in connection with spring 290. This assembly 550 comprises a first arm 552 extending through a slot 560 in the needle holder 200 and a second spring-bias 258 arm 554 extending through slot 208 in the interior boss 206. The ends of the respective arms are pivotally mounted at 557. Arm 554 is further pivotally mounted about pin 555 extending from the base of holder 200. Upon insertion of the needle assembly 100 within housing 204, arm 554 engages locking slot 154 so as to maintain the assembly 100 in place contra the spring 290 bias. Subsequent to use, user-depression of the pushbutton 556 at the end of arm 552 rotates the spring 258 biased arm 554 about pivot point 555 and out of the locking slot 154 (FIG. 20). Upon disengagement, the spring 290 bias ejects the needle assembly 100 from its housing 204.

FIG. 21 illustrates a locking lever 250/spring 290 combination as shown in FIGS. 1-5. However, the interior bore 207 of the housing 204 of the needle assembly has been tapered to receive a tapered hub 150, therein. These complementary configurations enhance the slidable action and fit of the needle assembly 100 within housing 204.

Figure 24:
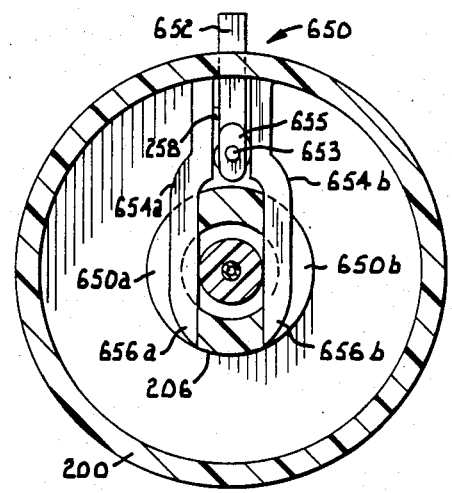
FIG. 24 is a sectional, elevation view, taken along lines 24—24 in FIG. 23 and on an enlarged scale, illustrating the cam-type locking mechanism in an engaged position with the needle assembly.
Figure 25:
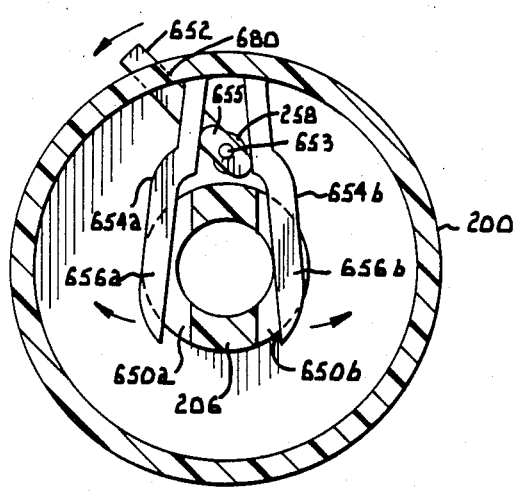
FIG. 25 illustrates the movement of the cam-type locking device of FIG. 24 towards a disengaged position.

FIGS. 23-25 illustrate a cam operated locking lever assembly 650. This assembly 650 comprises a user-operable spring 258 biased locking arm 652 extending through slot 680 in the needle holder 200. The interior end of arm 652 is pivotally mounted at 653 and includes a pivotal, elongated lobe 655 thereon. A pair of flexible, locking arms 654a and 654b extend from the interior of the needle holder 200 and include portions 656a and 656b which normally extend into the bore 207 of housing 204 via slots 650a and 650b. These locking flanges 656a, 656b engage the locking slot 154 of the needle assembly 100 upon insertion into housing 204. Subsequent to use, the arm 652 is user-movable through slot 680, as shown in FIG. 25, which pivots the elongated lobe 655 about pin 653 so as to bear against the arms 654a, 654b. This lobe 655/arm 654 relationship displaces the locking flanges 656a, 656b from the annular slot 154. Once disengaged, the needle assembly 100 is ejected from the housing 204 by the spring-bias 290.

Figure 26:
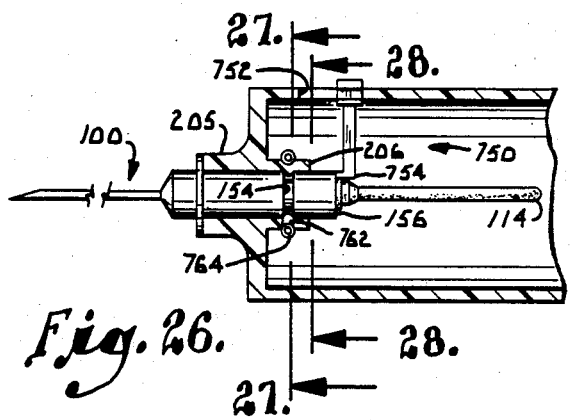
FIG. 26 is a fragmentary, sectional view illustrating an engaged needle assembly, as held in place by an alternative locking ring, as illustrated in FIGS. 27-28, and used in connection with a slidable locking lever illustrated in FIGS. 7-10.
Figure 27:
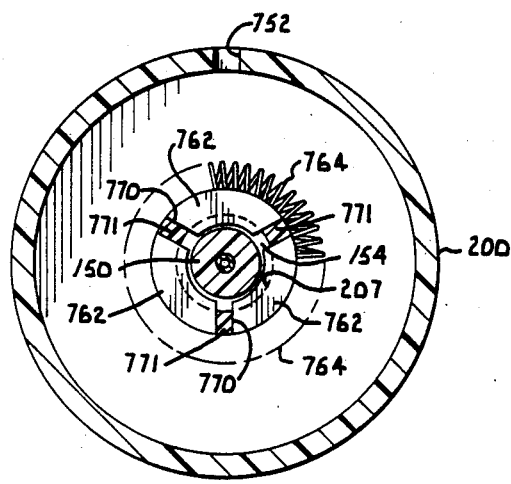
FIG. 27 is a sectional elevation view taken along lines 27—27 in FIG. 26 and illustrating the engagement of the ring with the locking slot of the needle assembly.
Figure 28:
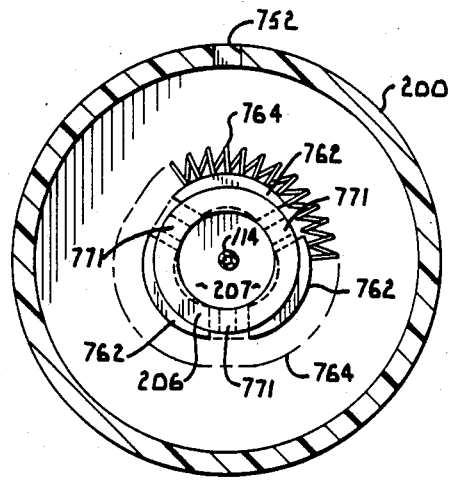
FIG. 28 is a view, taken along lines 28—28 in FIG. 26, illustrating the locking ring in a disengaged/released position and release of the needle assembly from its housing.

FIGS. 26-28 illustrate the use of a locking ring 760 in connection with a lever 750, slidable through slot 752, similar to that shown in FIGS. 9-10. The locking ring 760 includes an interior, three-piece, split ring 762 with an annular spring 764 bias therearound. (Spring 764 partially shown). The ring 760 is mounted about the exterior of the interior boss 206 such that portions of the split ring 762 are normally biased by spring 764 into the interior bore 207 of the housing 204 via rib-separated 771 annular slot 770 therearound (FIG. 28). Upon insertion of the needle assembly into the housing 204, the hub 150 overcomes the bias of spring 764 so as to urge the ring 762 out of the bore 207 allowing for passage of hub 150 therethrough (FIG. 28). Upon insertion of the needle assembly into the housing 204, the hub 150 overcomes the bias of spring 764 so as to urge the ring 762 out of the bore 207 allowing for passage of hub 150 therethrough (FIG. 28). Upon alignment of the locking slot 154 with slot 770, ring 762 extends therein holding the needle assembly 100 in housing 204. (It is noted that spring 764 may surround the housing 204 and annular rim 355 in FIG. 7. By making the housing 204 out of a resilient material, the spring will further bias rim 355 into slot 154.)

Upon locking, arm 754 of lever 750 bears against an end 156 of the needle hub 150. Subsequent to use, the lever 750 is user-slidable along slot 752 causing arm 754 to urge the needle assembly 100 from housing 204. This movement overcomes the bias offered by the spring 764 surrounding the locking ring 762 so as to disengage the three-part ring 762 from the locking slot 154 and release of the needle assembly 100 from its housing 204. Movement of the hub 150 through the housing non-uniformly compresses spring 764 as shown in FIG. 28. Upon release of the needle assembly 100 the spring 764 returns to its relaxed FIG. 27 position.

FIGS. 29–35 illustrate an alternative form of a cam-operated lever assembly 850. This assembly 850 comprises a user-operable locking arm 852 extending through slot 880 in the needle holder 200'. The arm 852 is pivotally mounted about pin 853 and includes a lobe-like interior end 855 and a user-operable exterior end 857 relative to holder 200'.

The holder 200' presents an exterior boss 205' with a bore 207' therein The boss 205'/bore 207, combination serves as a housing 204' for the needle assembly 100a/-cannula structure.

The needle assembly 100a/cannula structure is similar to that assembly 100 shown in FIG. 1. As such the assembly 100a comprises a cannula 110 having a front end 112 for venipuncture and a covered 116 rear end 112 for insertion through the membrane 302 of the stopper 304 of the evacuated collection tube 300. A removable cover (not shown) encloses the front end 112 of the needle 110 prior to use.

An intermediate hub 150a surrounds the needle 110 and includes a stop ring 152a and a locking slot 154a about the hub 150a. The beveled hub 150a includes a beveled top surface 156a and is of a reduced complimentary configuration relative to the bore 207' configuration in boss 205'.

FIGS. 31–35 illustrate the elements of the bias means and cam-operated locking assembly 850. This latter assembly 850 comprises the user-operable locking arm 852 extending through a slot 880 in the needle holder 200, which operates the locking ring 890. The interior end of arm 852 is pivotedly mounted about a pin 853.

The locking ring 890 is positioned within the holder 200 atop the interior base 201 and beneath support base 891. The ring 890 is of a resilient material and presents a pair of flexible locking flanges 856a, 856b. These flanges 856a, 856b are configured to present an orifice 866 which is aligned with the bore 207, The edges of the flanges 856a, 856b which form the orifice 866 are designated as 866a, 866b, 866c, 866d. These edges engage the female locking slot 154a hub of 150a upon insertion of the needle assembly 100a into the housing 204, as formed by the boss 205'/bore 207' combination.

Fastened atop the support base 891 is a bias ring 870 made of a resilient material. Ring 870 has a generally circular configuration and includes first and second resilient tabs 872, 74 which have a normal/relaxed depending position relative to the planar surface 876 of ring 870 as shown in FIG. 35.

In use the hub 150a of the cannula structure 100a is slidably inserted into the bore 207' of housing 204' with the rear cannula end 114 extending through orifice 866. The beveled hub's top surface 156a allows for the edges 866a, 866b, 866c, 866d to slide down the slanted walls 157a of hub 150a during the initial penetration of the hub 150a through the locking orifice 866. During this action the slanted walls 157a further spread the locking flanges 856a, 856b apart from their normal spread-apart position to a position similar to that shown in FIG. 34. Upon further insertion of the hub 150a into the housing 204a the male elements 866a, 866b, 866c, 866d engage the female locking slot 154a as the resilient locking flanges 856a, 856b to return to a normal/relaxed position. This position locks the flange edges 866a, 866b, 866c, 866d within the slot 154a as shown in FIG. 33. This engagement locks the hub 150a in the housing 204' with the front and rear ends 112, 114 of the needle 110 in their respective forward and rearward extensions beyond the housing 204'.

Concurrently, as shown in FIG. 31, the hub top 156a bears against the bottom of the bias tabs 872, 874 so as to upwardly displace the same from their normal depending/relaxed FIG. 35 position to the FIG. 32 position. Support base 891 receives forces acting against the ring 870 during tab 872 874 displacement. The resulting bias of these tabs 950, 952 against the top 156a of the cannula hub 150a urges the structure 100a from the housing 204'. The bias is overcome by the above-described engagement of the male locking flanges 856a, 856b within the female slot 154a. The blood drawing device is then used in a conventional blood-drawing manner.

Subsequent to use the needle assembly/cannula structure 100a is disposed by the user. As such the user slides the operating end of the arm 852 along the slot 880. This movement pivots arm 852 about pin 853 such that the opposed interior end 855 of ar 852 moves from its FIG. 33 position to a FIG. 34 position. This action spreads the locking flanges 856a, 856b and male elements 866a, 866b, 866c, 866d apart which displaces the latter from their locking position within the female locking slot 154a. Upon such release the tabs 950, 952 return to their normal/relaxed FIG. 35 position. This tab movement acts as a bias against the top 156a of hub 150a which urges the cannula structure 100a from its housing 204' for disposal. Thus the user need not handle the cannula structure 100a during disposal.

FIGS. 36–40 illustrate another alternative embodiment utilizing my above described concepts. Again a needle assembly/cannula structure 100b has a needle 110 with forwardly and rearwardly extending needle ends 110, 114 surrounded by a central hub 150b. The hub 150b has a vertically extending key slot 910, an annular female slot 154b and a top slot 986. Key slot 910 engages the key 912 extending along the surface of the bore 207c/boss 205c combination which forms housing 204c.

Extending through slot 904 in the holder 200 along the a base 201 thereof is a locking/bias mechanism 950. The one piece mechanism 950 includes a horizontally shiftable locking arm 960 and a vertically movable bias arm 980 as connected by an annular wire 952 extending about the inside circumference of holder 200. The structure 950 is made of a resilient wire. As shown in FIG. 38 the locking arm 960 comprises a user/operable end 962 extending to the outside of the holder 200 through slot 904. The arm 960 includes a curved male locking element 964, centrally located along the arm 960. The element 964 during its normal/relaxed position is located above the bore 207c as shown in phantom lines in FIG. 37. Horizontal movement of the user-operable end 962 of arm 960 through slot 904 displaces the male element 964 from its normal/relaxed FIG. 37 position to a displaced FIG. 38 position relative to the bore 207c of the housing 204c. The bias arm 980 includes an articulated portion 982 which normally extends across the bore 207c of the housing 204c (FIG. 38). This arm 980 has a normal/relaxed position, adjacent surface 201 as shown in FIG. 40, and a displaced position, relative to surface 201, as shown in FIG. 39.

Upon insertion of the hub 150b into the housing 204c the key 912 is positioned within the slot 910. During this keyed insertion the beveled top surface 157b of the hub displaces the locking element 964 from its normal/-relaxed position. Once the annular slot 154b is aligned with the locking element 964 the male element 964 is allowed to return to its normal/relaxed position. As such the element 964 is positioned within the slot 154b a shown in FIG. 37. This engagement locks the cannula structure 100b within the housing 204c for conventional use.

Concurrently the wire bias 982 engages the slot 986 atop the hub 150b. This action displaces the spring 980 from its FIG. 40 relaxed position to a FIG. 39 position. The spring 980 bias towards its normal FIG. 40 position urges the cannula structure 100b from the housing 204c. The engagement of male element 964 with the slot 154b prevents such cannula movement.

Subsequent to use the user slides the operable end 962 of the locking arm 960 through the slot 904 to the FIG. 3 position. This action disengages the male locking element 964 from the female locking slot 154b. Once removed the spring 980 bias acting atop the hub 154b of the cannula structure 100b causes discharge of the needle assembly/cannula structure 100b from the housing 204c for disposal. Thus again the user need not handle the cannula structure during disposal.

Although I have shown various particular combinations of locking assemblies/bias means hereinabove, it is understood that other combinations may be utilized.

Also, it is to be understood that while certain forms of this invention have been illustrated and described, it is not limited thereto, except in so far as such limitations are included in the following claims.

Having thus described the invention, what is claimed as new and desired to be secured by Letters Patent is:

1. A fluid collection system comprising:
    a double-ended cannula structure open at both ends and having a bore for passage of fluid therethrough;
    a holder having means therein for releasably mounting the cannula structure with one end extending forwardly for venipuncture and the other end extending rearwardly for
    coupling with a collection container, said mounting means comprising:
        housing means for receiving a portion of said structure therein; and
        user-operable locking means for releasably engaging said cannula structure upon insertion of said structure in said housing means, said engagement maintaining said cannula structure in said housing means during use said locking means comprising:
            female means associated with said cannula structure for receiving a complementary male element comprising:
                a hub intermediate said ends of said structure for insertion in said housing means;
                a slot in said hub for reception of said complementary male element therein;
            male means including said male element for engagement with said slot, said male means comprising:
                a locking ring comprising first and second opposed locking flanges for presenting said male element;
                means for mounting said locking ring within said holder, whereupon said flanges engage said slot upon said reception of said structure in said housing means;
        means for moving said locking flanges to a spaced-apart relationship out of said slot, whereby to release said cannula structure from said housing means.

2. The apparatus as claimed in claim 1 wherein said moving means comprises:
    an arm member having first and second ends with said first end positioned between said locking flanges and said second and extending outside said holder;
    means for pivotally mounting said arm whereupon user movement of said second end causes movement of said first end in a direction to displace said flanges from said spaced apart relationship out of said slot.

3. The apparatus as claimed in claim 1 further comprising bias means for urging said structure from said housing means upon displacement of said flanges from said slot.

4. The apparatus as claimed in claim 3 wherein said bias means comprises:
    a plate having at least one resilient tab element therein, said tab having a first relaxed position and a second displaced position;
    means for mounting said plate atop said locking ring, said tab being displaced from said relaxed position upon insertion of said structure within said housing means, said displaced tab urging said structure from said housing means.

* * * * *